(12) United States Patent
Sharma et al.

(10) Patent No.: US 9,107,609 B2
(45) Date of Patent: *Aug. 18, 2015

(54) INTER-FRAME COMPLEX OCT DATA ANALYSIS TECHNIQUES

(71) Applicant: Carl Zeiss Meditec, Inc., Dublin, CA (US)

(72) Inventors: Utkarsh Sharma, San Leandro, CA (US); Matthew J. Everett, Livermore, CA (US); Lingfeng Yu, Rancho Santa Margarita, CA (US)

(73) Assignee: Carl Zeiss Meditec, Inc., Dublin, CA (US)

( * ) Notice: Subject to any disclaimer, the term of this patent is extended or adjusted under 35 U.S.C. 154(b) by 236 days.

This patent is subject to a terminal disclaimer.

(21) Appl. No.: 13/854,623

(22) Filed: Apr. 1, 2013

(65) Prior Publication Data

US 2013/0289882 A1  Oct. 31, 2013

Related U.S. Application Data

(63) Continuation of application No. 13/543,373, filed on Jul. 6, 2012, now Pat. No. 8,433,393.

(60) Provisional application No. 61/505,483, filed on Jul. 7, 2011.

(51) Int. Cl.
*A61B 5/00* (2006.01)
*A61B 3/10* (2006.01)
*A61B 5/026* (2006.01)

(52) U.S. Cl.
CPC ............... *A61B 3/102* (2013.01); *A61B 5/0066* (2013.01); *A61B 5/0261* (2013.01)

(58) Field of Classification Search
CPC ...... A61B 3/102; A61B 5/0066; A61B 5/0261
USPC ......................................................... 600/477
See application file for complete search history.

(56) References Cited

U.S. PATENT DOCUMENTS 6,549,801 B1   4/2003   Chen et al.
7,301,644 B2   11/2007  Knighton et al.
(Continued)

FOREIGN PATENT DOCUMENTS

WO   2010/030159 A2   3/2010
WO   2010/129494 A2   11/2010
(Continued)

OTHER PUBLICATIONS

Non-Final Office Action received for U.S. Appl. No. 13/781,375, mailed on Jun. 20, 2014, 18 pages.
(Continued)

*Primary Examiner* — Jonathan Cwern
(74) *Attorney, Agent, or Firm* — Morrison & Foerster LLP

(57) ABSTRACT

Techniques for collecting and processing complex OCT data to detect localized motion contrast information with enhanced accuracy and sensitivity are presented. In a preferred embodiment, vector differences between complex OCT signals taken at the same location on the sample are used to detect blood flow in the retina. Additional embodiments involving non-linear intensity weighting of the motion contrast information, normalization of the vector difference amplitudes, and calculating the absolute value of the standard deviation of Doppler signal are described. Image processing techniques to enhance the images resulting from these motion contrast techniques are also presented.

25 Claims, 4 Drawing Sheets

(56) References Cited

U.S. PATENT DOCUMENTS

| | | | |
|---|---|---|---|
| 7,359,062 | B2 | 4/2008 | Chen et al. |
| 8,079,711 | B2 | 12/2011 | Stetson et al. |
| 2003/0208326 | A1 | 11/2003 | Chen et al. |
| 2004/0076262 | A1 | 4/2004 | Shao et al. |
| 2005/0171438 | A1 | 8/2005 | Chen et al. |
| 2007/0019846 | A1 | 1/2007 | Bullitt et al. |
| 2008/0025570 | A1 | 1/2008 | Fingler et al. |
| 2008/0100612 | A1 | 5/2008 | Dastmalchi et al. |
| 2008/0159604 | A1 | 7/2008 | Wang et al. |
| 2008/0291463 | A1 | 11/2008 | Milner et al. |
| 2009/0005693 | A1 | 1/2009 | Brauner et al. |
| 2009/0268162 | A1 | 10/2009 | Stetson et al. |
| 2009/0270738 | A1 | 10/2009 | Izatt et al. |
| 2010/0027857 | A1 | 2/2010 | Wang |
| 2010/0113900 | A1 | 5/2010 | Shakespeare et al. |
| 2010/0159497 | A1 | 6/2010 | Kimia et al. |
| 2010/0189334 | A1 | 7/2010 | Tomidokoro et al. |
| 2010/0240986 | A1 | 9/2010 | Stiles |
| 2010/0245770 | A1 | 9/2010 | Zhang et al. |
| 2011/0034803 | A1 | 2/2011 | Stetson |
| 2011/0063573 | A1 | 3/2011 | Meyer et al. |
| 2011/0103657 | A1 | 5/2011 | Kang et al. |
| 2011/0109881 | A1 | 5/2011 | Munger et al. |
| 2011/0164791 | A1 | 7/2011 | Bajraszewski et al. |
| 2011/0169978 | A1 | 7/2011 | Lasser et al. |
| 2011/0243408 | A1 | 10/2011 | Takama |
| 2012/0035454 | A1 | 2/2012 | Tearney et al. |
| 2012/0053904 | A1 | 3/2012 | Yuasa et al. |
| 2012/0063665 | A1 | 3/2012 | Wang et al. |
| 2012/0075638 | A1 | 3/2012 | Rollins et al. |
| 2012/0120408 | A1 | 5/2012 | Yasuno et al. |
| 2012/0140171 | A1 | 6/2012 | Hirose et al. |
| 2012/0218517 | A1 | 8/2012 | Imamura |
| 2012/0274745 | A1 | 11/2012 | Russell |
| 2012/0277570 | A1 | 11/2012 | Todor et al. |
| 2013/0018254 | A1 | 1/2013 | Drucker |
| 2013/0094725 | A1 | 4/2013 | Gulsun et al. |
| 2013/0215235 | A1 | 8/2013 | Russell |
| 2014/0049632 | A1 | 2/2014 | Hemmer |
| 2014/0293222 | A1 | 10/2014 | Coelho et al. |

FOREIGN PATENT DOCUMENTS

| | | |
|---|---|---|
| WO | 2010/131944 A2 | 11/2010 |
| WO | 2010/138645 A2 | 12/2010 |
| WO | 2010/129494 A3 | 2/2011 |
| WO | 2011/097631 A2 | 8/2011 |
| WO | 2011/097631 A3 | 11/2011 |

OTHER PUBLICATIONS

Herfkens, Robert, "Computational Visualization of 4D Cardiac Flow", Available at <http://www.nvidia.com/object/quadro-fermi-video-view04.html>, 2010, 1 page.

Makita et al., "Optical Coherence Angiography for the Eye", SPIE, 2009, pp. 1-3.

Al-Diri et al., "Automated Analysis of Retinal Vascular Network Connectivity", Computerized Medical Imaging and Graphics, vol. 34, 2010, pp. 462-470.

An et al., "Optical Microangiography Provides Correlation between Microstructure and Microvasculature of Optic Nerve Head in Human Subjects", Journal of Biomedical Optics, vol. 17, No. 11, Nov. 2012, pp. 116018-1-116018-6.

Avakian et al., "Fractal Analysis of Region-based Vascular Change in the Normal and Non-Proliferative Diabetic Retina", Current Eye Research, vol. 24, No. 4, 2002, pp. 274-280.

Ganesan et al., "Development of an Image-Based Network Model of Retinal Vasculature", Annals of Biomedical Engineering, vol. 38, No. 4, Apr. 2010, pp. 1566-1585.

Jia et al., "Quantitative OCT Angiography of Optic Nerve Head Blood Flow", Biomedical Optics Express, vol. 3, No. 12, 2012, pp. 3127-3137.

John et al., "Dimensions of the Foveal Avascular Zone using the Heidelberg Retinal Angiogram-2 in Normal Eyes", Indian Journal of Ophthalmology, vol. 59, No. 1, 2011, 6 pages.

Kim et al., "In vivo Volumetric Imaging of Human Retinal Circulation with Phase-Variance Optical Coherence Tomography", Biomedical Optics Express, vol. 2, No. 6, 2011, pp. 1504-1513.

Kim et al., "Noninvasive Imaging of the Foveal Avascular Zone with High-Speed, Phase-Variance Optical Coherence Tomography", Investigative Ophthalmology & Visual Science, vol. 53, No. 1, Jan. 2012, pp. 85-92.

International Search Report and Written Opinion received for PCT Patent Application No. PCT/EP2013/059560 mailed on Aug. 27, 2013, 6 pages.

Popovic et al., "Noninvasive Imaging of Human Foveal Capillary Network Using Dual-Conjugate Adaptive Optics", Investigative Ophthalmology & Visual Science, vol. 52, No. 5, Apr. 2011, pp. 2649-2655.

Ramezani et al., "Agreement Between Clinical Estimation and a New Quantitative Analysis by Photoshop Software in Fundus and Angiographic Image Variables", Int. Ophthalmol, vol. 29, 2009, pp. 439-449.

Schmoll et al., "Imaging of the Parafoveal Capillary Network and its Integrity Analysis using Fractal Dimension", Biomedical Optics Express, vol. 2, No. 5, 2011, pp. 1159-1168.

Spaide et al., "Fundus Autofluorescence and Central Serous Chorioretinopathy", American Academy of Ophthalmology, vol. 112, No. 5, May 2005, pp. 825-833.

Wang et al., "Imaging Retinal Capillaries Using Ultrahigh-Resolution Optical Coherence Tomography and Adaptive Optics", Investigative Ophthalmology & Visual Science, vol. 52, No. 9, Aug. 2011, pp. 6292-6299.

Zheng et al., "Automated Segmentation of Foveal Avascular Zone in Fundus Fluorescein Angiography", Investigative Ophthalmology & Visual Science, vol. 51, No. 7, Jul. 2010,, pp. 3653-3659.

Non Final Office Action received for U.S. Appl. No. 13/543,373, mailed on Sep. 25, 2012, 9 pages.

Notice of Allowance received for U.S. Appl. No. 13/543,373, mailed on Jan. 2, 2013, 5 pages.

An et al., "In vivo Volumetric Imaging of Vascular Perfusion within Human Retina and Choroids with Optical Micro-Angiography", Optics Express, vol. 16, No. 15, Jul. 21, 2008, pp. 11438-11452.

An et al., "Ultrahigh Sensitive Optical Microangiography for in vivo Imaging of Microcirculations within Human Skin Tissue Beds", Optics Express, vol. 18, No. 8, Apr. 12, 2010, pp. 8220-8228.

Fingler et al., "Mobility and Transverse Flow Visualization using Phase Variance Contrast with Spectral Domain Optical Coherence Tomography", Optics Express, vol. 15, No. 20, Oct. 1, 2007, pp. 12636-12653.

Fingler et al., "Volumetric Microvascular Imaging of Human Retina using Optical Coherence Tomography with a Novel Motion Contrast Technique", Optics Express, vol. 17, No. 24, Nov. 23, 2009, pp. 22190-22200.

Kirkpatrick et al., "OCT-Based Elastography for Large and Small Deformations", Optics Express, vol. 14, No. 24, Nov. 27, 2006, pp. 11585-11597.

Leitgeb et al., "Real-Time Assessment of Retinal Blood Flow with Ultrafast Acquisition by Color Doppler Fourier Domain Optical Coherence Tomography", Optics Express, vol. 11, No. 23, Nov. 17, 2003, pp. 3116-3121.

Leitgeb et al., "Ultrahigh Resolution Fourier Domain Optical Coherence Tomography", Optics Express, vol. 12, No. 10, May 17, 2004, pp. 2156-2165.

Liu et al., "Intensity-Based Modified Doppler Variance Algorithm: Application to Phase Instable and Phase Stable Optical Coherence Tomography Systems", Optics Express, vol. 19, No. 12, Jun. 6, 2011, pp. 11429-11440.

Makita et al., "Comprehensive in vivo Micro-Vascular Imaging of the Human Eye by Dual-Beam-Scan Doppler Optical Coherence Angiography", Optics Express, vol. 19, No. 2, Jan. 17, 2011, pp. 1271-1283.

Makita et al., "Optical Coherence Angiography", Optics Express, vol. 14, No. 17, Aug. 21, 2006, pp. 7821-7840.

(56) References Cited

OTHER PUBLICATIONS

Mariampillai et al., "Optimized Speckle Variance OCT Imaging of Microvasculature", Optics Letters, vol. 35, No. 8, Apr. 15, 2010, pp. 1257-1259.

Schmitt, Joseph M., "OCT Elastography: Imaging Microscopic Deformation and Strain of Tissue", Optics Express, vol. 3, No. 6, Sep. 14, 1998, pp. 199-211.

Wang et al., "Depth-Resolved Imaging of Capillary Networks in Retina and Choroid using Ultrahigh Sensitive Optical Microangiography", Optics Letters, vol. 35, No. 9, May 1, 2010, pp. 1467-1469.

Wang et al., "Frequency Domain Phase-Resolved Optical Doppler and Doppler Variance Tomography", Optics Communications, vol. 242, 2004, pp. 345-350.

Wang et al., "Three Dimensional Optical Angiography", Optics Express, vol. 15, No. 7, Apr. 2, 2007, pp. 4083-4097.

White et al., "In vivo Dynamic Human Retinal Blood Flow Imaging using Ultra-High-Speed Spectral Domain Optical Doppler Tomography", Optics Express, vol. 11, No. 25, Dec. 15, 2003, pp. 3490-3497.

Yazdanfar et al., "Imaging and Velocimetry of the Human Retinal Circulation with Color Doppler Optical Coherence Tomography", Optics Letters, vol. 25, No. 19, Oct. 1, 2000, pp. 1448-1450.

Zhao et al., "Doppler Standard Deviation Imaging for Clinical Monitoring of in vivo Human Skin Blood Flow", Optics Letters, vol. 25, No. 18, Sep. 15, 2000, pp. 1358-1360.

Zotter et al., "Visualization of Microvasculature by Dual-Beam Phase-Resolved Doppler Optical Coherence Tomography", Optics Express, vol. 19, No. 2, Jan. 17, 2011, pp. 1217-1227.

International Preliminary Report on Patentability received for PCT Patent Application No. PCT/EP2013/059560, mailed on Nov. 20, 2014, 8 pages.

Final Office Action received for U.S. Appl. No. 13/781,375, mailed on Mar. 3, 2015, 14 pages.

INTER-FRAME COMPLEX OCT DATA ANALYSIS TECHNIQUES

PRIORITY

This application is a Continuation of U.S. patent application Ser. No. 13/543,373, filed Jul. 6, 2012, which claims priority to U.S. Provisional Application Ser. No. 61/505,483 filed Jul. 7, 2011 hereby incorporated by reference.

TECHNICAL FIELD

One or more embodiments of the present invention relate to the field of optical coherence tomography. In particular, the invention described herein describes systems and methods for detecting and displaying localized motion in a sample under investigation.

BACKGROUND

Optical coherence tomography (OCT) is a noninvasive, noncontact imaging modality that uses coherence gating to obtain high-resolution cross-sectional images of tissue microstructure. In Fourier domain OCT (FD-OCT), the interferometric signal between light from a reference and the back-scattered light from a sample point is recorded in the frequency domain rather than the time domain. After a wavelength calibration, a one-dimensional Fourier transform is taken to obtain an A-line spatial distribution of the object scattering potential. The spectral information discrimination in FD-OCT is accomplished either by using a dispersive spectrometer in the detection arm in the case of spectral-domain OCT (SD-OCT) or rapidly tuning a swept laser source in the case of swept-source OCT (SS-OCT). The axial or depth resolution of the FD-OCT system is determined by the actual spectral width recorded and used for reconstruction. The axial range over which an OCT image is taken (imaging depth, scan depth or imaging range) is determined by the sampling interval or resolution of the optical frequencies recorded by the OCT system.

Functional OCT can provide important clinical information that is not available in the typical intensity based structural OCT images. There have been several functional contrast enhancement methods including Doppler OCT, Phase-sensitive OCT measurements, Polarization Sensitive OCT, etc. Integration of functional extensions can greatly enhance the capabilities of OCT for a range of applications in medicine. One of the most promising functional extensions of OCT has been the field of OCT angiography which is based on flow contrast. The field of OCT angiography has generated a lot of interest in the OCT research community during the last few years. There are several flow contrast techniques in OCT imaging that utilize inter-frame change analysis of the OCT intensity or phase-resolved OCT data. One of the major applications of such techniques has been to generate en face vasculature images of the retina. En face images are typically generated from three dimensional data cubes by summing pixels along a given direction in the cube, either in their entirety or from sub-portions of the data volume (see for example U.S. Pat. No. 7,301,644). Visualization of the detailed vasculature using OCT could enable doctors to obtain new and useful clinical information for diagnosis and management of eye diseases in a non-invasive manner. Fluorescein angiography and indocyanine green (ICG) angiography are currently the gold standards for vasculature visualization in the eye. However, the invasiveness of the approach combined with possible complications (allergy to dyes, side effects) make it an unsuitable technique for widespread screening applications in ophthalmic clinics.

Vasculature can be visualized by OCT using the effect of motion caused by blood flow on the backscattered light. Doppler-OCT has been used for more than a decade to provide contrast due to blood flow. However, Doppler OCT, despite being capable of quantifying blood flow, has several limitations such as limited dynamic range and dependence of Doppler signal on the angle of probe beam and flow direction. In addition, the pulsatile nature of blood flow can also affect the Doppler signal. Chen et al. demonstrated the use of the Doppler variance technique for the first time to obtain vasculature mapping (see for example Y. Zhao et al. Doppler standard deviation imaging for clinical monitoring of in vivo human skin blood flow," Optics Letters 25, 1358-1360 (2000)). Doppler variance, while incapable of quantifying the blood flow, is less sensitive to the Doppler angle and the pulsatile nature of the blood flow. Hence Doppler variance provides better detection for the location of the blood flow. Makita et al. used phase-resolved Doppler OCT to perform OCT vasculature mapping of the human retina (S. Makita et al. "Optical Coherence Angiography," Optics Express 14, 7821-7840 (2006)). R. K. Wang et al. developed a technique, optical microangiography (OMAG), that applies a constant modulation frequency to the interferograms formed between reference and sample beams to separate the static and moving elements using mathematical properties of Hilbert and Fourier transformations applied on real valued interferometric data. This resulted in separation of the vasculature image (due to motion of blood flow) and the tissue image (see for example R. K. Wang et al. "Three dimensional optical angiography," Optics Express 15, 4083-4097 (2007) and L. An et al., "In vivo volumetric imaging of vascular perfusion within human retina and choroids with optical microangiography," Optics Express 16, 11438-11452 (2008)). Wang et al. claimed improved sensitivity for microvasculature flow measurements using a technique called ultrahigh sensitive OMAG (UHS-OMAG). In this technique, Wang et al. applied the OMAG technology along the slow scan axis, i.e. the time separation between two measurements was now determined by B-frame rate rather than A-scan rate (see for example R. K. Wang et al., "Depth-resolved imaging of capillary networks in retina and choroid using ultrahigh sensitive optical microangiography," Optics Letters, 35(9), 1467-1469 (2010) and L. An et al., "Ultrahigh sensitive optical microangiography for in vivo imaging of microcirculations within human skin tissue beds," Optics Express, 18(8), 8220-8228 (2010)). However, this method requires higher post-processing computational load and some of the UHS-OMAG methods added hardware complexity to the system. Fingler et al. performed Doppler or phase variance based detection by comparing the phase data at the same location from multiple B-scans or frames (see for example J. Fingler et al., "Mobility and transverse flow visualization using phase variance contrast with SD-OCT," Optics Express 15, 12636-12653 (2007), J. Fingler et al., "Volumetric microvascular imaging of human retina using OCT with a novel motion contrast technique," Optics Express 17, 22190-22200 (2009) and US Patent Publication No. 2008/0025570). Because inter-frame analysis was used instead of comparing subsequent A-scans, Fingler et al. produced improved vasculature images compared to the results obtained by Chen et al. The Inter-frame analysis used by Fingler et al. allowed increased time difference between two OCT measurements at the same location and hence increased the sensitivity to slower flow. Inter-frame analysis using OCT B-scan images to measure small displacements was also previously used for research studies in OCT elastography (see for example J. M.

Schmitt, "OCT elastography: imaging microscopic deformation and strain of tissue," Optics Express 3, 199-211 (1998) and S. J. Kirkpatrick, R. K. Wang, and D. D. Duncan, "OCT-based elastography for large and small deformations," Optics Express 14, 11585-11597 (2006). Fingler's inter-frame phase variance analysis method relies only on the phase information in the OCT data to detect motion. One of the limitations of phase only methods is that phase signals have increased error in measurements at low backscattered signal intensity. The OCT data obtained from the light backscattered from the moving scattering particles has variations in intensity as well as the phase. Mariampillai et al. confirmed this by performing vasculature imaging based on inter-frame speckle variance analysis (see for example A. Mariampillai et al. Optimized speckle variance OCT imaging of microvasculature," Optics Letters 35, 1257-1259 (2010)).

SUMMARY

In light of the limitations in the prior art, we propose here several new complex OCT data processing techniques to enhance the accuracy and sensitivity to detect localized motion contrast caused by blood flow. The OMAG techniques require high post-processing computational load and some require hardware complexity. Other techniques in the prior art either used just the phase information or intensity information alone derived from the complex OCT data to detect motion. The scattering properties of blood are very different from that of the other retinal tissues. The amplitude of the light backscattered from the tissue also provides useful information about their optical properties. In addition, noisy signal causes inherently high variations in the phase measurements leading to 'false positive' detection of motion. In our invention, we reduce the effect of errors in motion detection by using techniques that derive the motion-contrast information from the complex OCT signal, rather than just relying on intensity or phase alone. The techniques of the present invention including non-linear intensity weighting, vector difference, normalized vector difference amplitude, and absolute standard deviation of Doppler signal can generate motion-contrast data with high sensitivity and accuracy.

DETAILED DESCRIPTION

Figure 1:
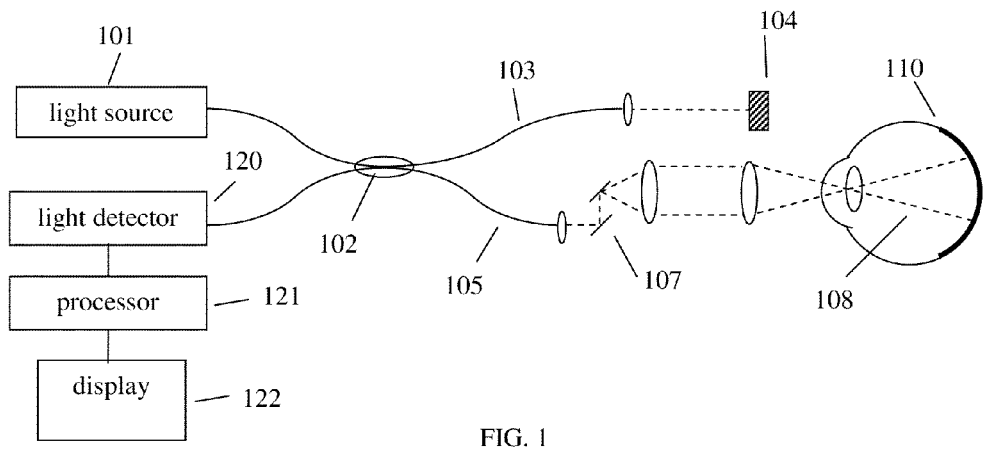
FIG. 1 illustrates the general components of an OCT system for ophthalmic imaging.

A diagram of a generalized FD-OCT system is shown in FIG. 1. Light from source 101 is routed, typically by optical fiber 105, to illuminate the sample 110, a typical sample being tissues in the human eye. The source 101 can be either a broadband light source with short temporal coherence length in the case of SD-OCT or a wavelength tunable laser source in the case of SS-OCT. The light is scanned, typically with a scanner 107 between the output of the fiber and the sample, so that the beam of light (dashed line 108) is scanned laterally (in x and y) over the area or volume to be imaged. Light scattered from the sample is collected, typically into the same fiber 105 used to route the light for sample illumination. Reference light derived from the same source 101 travels a separate path, in this case involving fiber 103 and retro-reflector 104 with an adjustable optical delay. Those skilled in the art recognize that a transmissive reference path can also be used and that the adjustable delay could be placed in the sample or reference arm of the interferometer. Collected sample light is combined with reference light, typically in a fiber coupler 102, to form light interference in a detector 120. Although a single fiber port is shown going to the detector, those skilled in the art recognize that various designs of interferometers can be used for balanced or unbalanced detection of the interference signal. The output from the detector is supplied to a processor 121. The results can be stored in the processor 121 or displayed on display 122. The processing and storing functions may be localized within the OCT instrument or functions may be performed on an external processing unit to which the collected data is transferred. This unit could be dedicated to data processing or perform other tasks which are quite general and not dedicated to the OCT device.

Figure 2:
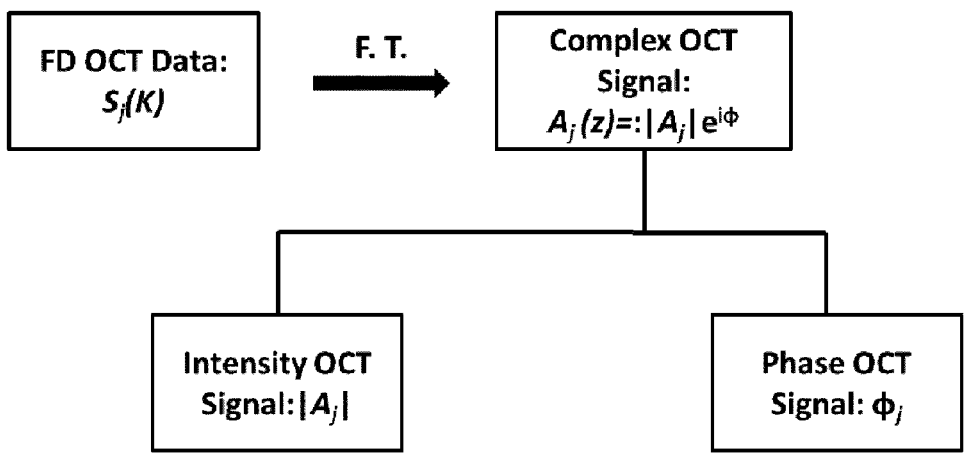
FIG. 2 shows the relationship between the intensity and phase information resulting from the Fourier Transform of detected OCT signal.
Figure 3:
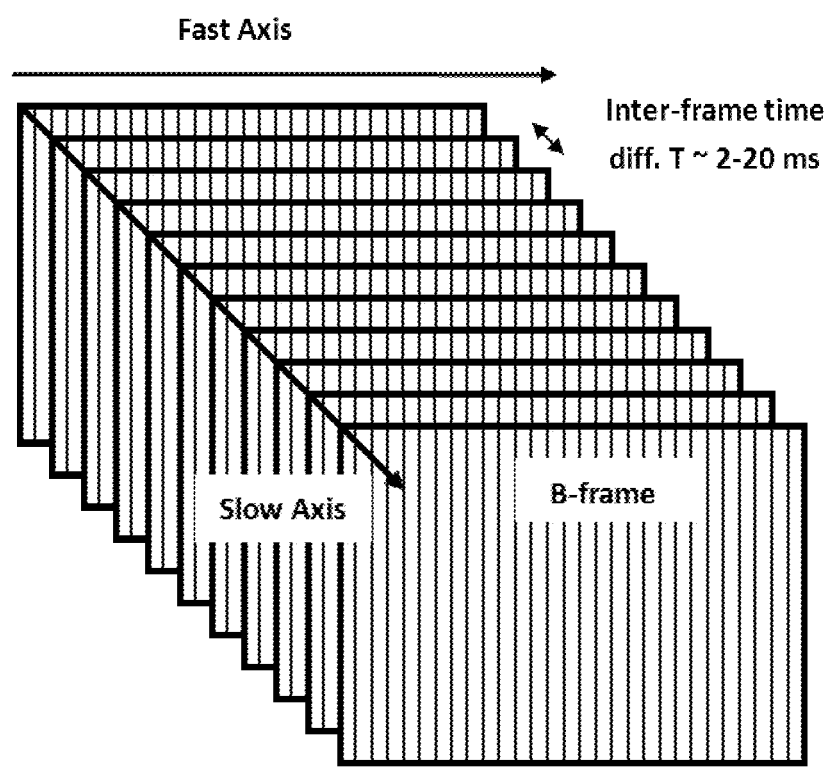
FIG. 3 illustrates a scanning configuration that can be used to collect motion contrast data.

In Fourier Domain optical coherence tomography (FD-OCT), each measurement is the real-valued spectral interferogram ($S_j(k)$). The real-valued spectral data typically goes through several postprocessing steps including background subtraction, dispersion correction, etc. The Fourier transform of the processed interferogram, results in a complex valued OCT signal output $A_j(z)=|A_j|e^{i\varphi}$ as shown in FIG. 2. The absolute value of this complex OCT signal, $|A_j|$, reveals the profile of scattering intensities at different path lengths, and therefore scattering as a function of depth (z-direction) in the sample (see for example Leitgeb et al. "Ultrahigh resolution Fourier domain optical coherence tomography," Optics Express 12(10):2156 2004). Similarly, the phase, $\varphi_j$, can also be extracted from the complex valued OCT signal. The profile of scattering as a function of depth is called an axial scan (A-scan). A set of A-scans measured at neighboring locations in the sample produces a cross-sectional image (tomogram or B-scan) of the sample. A set of B-scans collected at the same or closely spaced locations on the tissue can be used in motion contrast techniques. One such scanning protocol commonly referred to as MB scanning is shown in FIG. 3. Here a series of A-scans are collected along an axis (labeled Fast axis) to generate a B-scan. The scanning is repeated at the same or densely spaced locations over time (represented by the slow axis) referred to herein as cluster scans. An inter-frame comparison refers to comparing consecutive B-scans from approximately the same location. The inter-frame time difference between consecutive B-scans depends on the system speed (A-line rate), number of A-scans in a single B-scan and the time it takes to return to the start position (fly-back times) but is typically on the order of 2-20 ms.

For generating the enface images described herein, each B-scan in the given data volume consists of 300 A-scans, each cluster scan consists of four B-scans, for a total of eighty different cluster scans. Hence, the number of A-scans in a given unit data volume are 300×80×4. After processing the data to highlight motion contrast using a particular motion contrast technique as described herein, a range of 25-30 pixels corresponding to 50-60 microns of tissue depth from the surface of internal limiting membrane (ILM) in retina, are summed to generate an en face image of the vasculature. Each B-scan takes approximately 12 ms to acquire (including flyback time) so the time between B-scans is approximately 12 ms which is on the order of interest for retinal vasculature dynamics. This data set is illustrative in nature and one skilled in the art will appreciate that any type of OCT data in which OCT measurements are collected at the same or approximately the same location over relevant timescales for the motion being investigated could be used in the present invention.

The complex valued OCT signal for the scan-pattern illustrated in FIG. 3 can be represented as following: $B_j(z) = [A_{j1}(z) A_{j2}(z) A_{j3}(z) \ldots A_{jM}(z)]$. Here $B_j$ is the $j^{th}$ B-scan and can be described as a collection of a given number of A-scans over a transverse range (M A-scans in this case), and $A_{j1}(z)$ corresponds to the complex OCT signal for a given A-scan at a given depth (z). The complex valued OCT signal can be written as follows: $A_{jk}(z,t) = |A_{jk}(z,t)| e^{i\phi_{jk}(z,t)}$. Here $|A_{jk}(z,t)|$ is the amplitude of the complex signal and $\phi_{jk}(z,t)$ corresponds to the phase of the signal as in FIG. 2

As discussed above, Fingler et al. have described a phase-variance technique in which the variance of the phase-differences (Doppler signal) between consecutive B-scans was calculated to detect the motion. From a set of N repeated measurements separated by time T at the same location, N−1 measurements of bulk-motion corrected phase difference values are calculated as followed: $\Delta\phi_{jk}(z,t_{jk}) = \phi_{j+1k}(z,t_{jk}+T) - \phi_{jk}(z,t_{jk})$. Variance is calculated by using the N−1 set of values of phase changes $\{\Delta\phi_{jk}(z,t_{jk})\}_{j=1, 2 \ldots N-1}$. According to the standard mathematical definition, the variance of phase changes is calculated as follows:

$$\sigma^2_{\Delta\phi} = \frac{\sum_{j=1}^{N-1}(\Delta\phi_{jk}(z,t_{jk}) - \overline{\Delta\phi(z)})^2}{N-1}; \quad (1)$$

where $$\overline{\Delta\phi(z)} = \frac{\sum_{j=1}^{N-1}\Delta\phi_{jk}(z,t_{jk})}{N-1}.$$

It must be noted that Doppler frequency shift ($\omega$) is proportional to the phase change between two measurements and can be written as: $\omega = (\Delta\phi/T)$. Chen et al. calculate the Doppler variance as shown below:

$$\sigma^2_\omega = \frac{\int_{-\infty}^{+\infty}(\omega-\overline{\omega})^2 P(\omega)d\omega}{\int_{-\infty}^{+\infty}P(\omega)d\omega} = \frac{1}{T^2}\left(1 - \frac{\left|\sum_{j=1}^{N-1}A_{jk}A^*_{j+1k}\right|}{\sum_{j=1}^{N-1}A_{jk}A^*_{jk}}\right). \quad (2)$$

It must be noted that according to Fingler's definition, mean phase change $\overline{\Delta\phi(z)}$ is calculated independent of the OCT signal amplitude as shown in Equation 1. On the other hand, Chen et al. calculate the mean Doppler frequency ($\overline{\omega}$) or mean phase change ($\overline{\Delta\phi(z)}$) by an OCT signal intensity weighted averaging scheme as shown below:

$$\overline{\Delta\phi(z)} = T \cdot \overline{\omega} = \arg\left(\sum_{j=1}^{N-1} A_{jk} \cdot A^*_{j+1k}\right) = \tan^{-1}\left[\frac{\mathrm{Im}\left(\sum_{j=1}^{N-1}A_{jk} \cdot A^*_{j+1k}\right)}{\mathrm{Re}\left(\sum_{j=1}^{N-1}A_{jk} \cdot A^*_{j+1k}\right)}\right]. \quad (3)$$

Here T is the time difference between two successive measurements. For the Equations and simulations presented in this document, we have used the definition of mean phase shift as defined in Equation 3, unless specified otherwise.

Several new Inter-frame Complex OCT Data analysis techniques for motion detection will now be described. In each case, a collection of OCT measurement data would be acquired as described above with at least two measurements being made at the same location on the sample. The measurement data would be processed to generate a complex OCT signal having both intensity and phase information, that would then be used for motion contrast analysis according to one of the following techniques.

I. Non-linear Intensity Weighted Phase Resolved Techniques

The motion within the sample can lead to variations in amplitude (hence intensity) as well as phase in the complex OCT data. Techniques based only on the phase information derived from complex OCT signal reject the intensity data which can provide additional information and hence incorporation of this information can lead to improved images with better motion contrast. This is especially true for the noisy signal (or signal with low SNR) as it causes inherently high variations in the phase measurements leading to 'false positive' detection of motion. Also the optical scattering property of the blood is different from that of retinal tissues. Blood is a highly scattering medium and hence intensity (linear or non-linear) based motion-contrast weighting may better differentiate blood (scattering caused by moving cells) from the static tissue. In our invention, we reduce the effect of errors in phase measurements due to noisy signal by using an intensity based weighting factor. For example, the contributions due to phase variance information can be modified by using an intensity based weighting factor and later normalized as shown in the expression below:

$$\frac{\sum_{j=1}^{N-1} F(|A_{jk}(z)|, |A_{j+1k}(z)|) \cdot (\Delta\phi_{jk}(z,t_{jk}) - \overline{\Delta\phi(z)})^2}{C_2 + \sum_{j=1}^{N-1} F(|A_{jk}(z)|, |A_{j+1k}(z)|)}. \quad (4)$$

Here $F(|A_{jk}(z)|, |A_{j+1k}(z)|)$ is the signal amplitude based weighting function that can be used to reduce the contribution of large phase variance resulting from noisy data. In the preferred embodiment, the weighting function increases monotonically from zero with increasing signal amplitude, and $C_2$ is a constant that causes this formula to drop toward zero as the OCT signal becomes small, thereby eliminating noise associated with low signal. The weighting function could be a continuous and smoothly varying function such as Sigmoid functions. One of the preferred embodiments of the smoothly varying weighting function is shown in Equation 5 below:

$$F(|A_{jk}(z)|, |A_{j+1k}(z)|) = \frac{C_1 \cdot |A_{jk}(z)|^\alpha \cdot |A_{j+1k}(z)|^\alpha}{|A_{jk}(z)|^\alpha \cdot |A_{j+1k}(z)|^\alpha + C_3 |A_{th}|^{2\alpha}}. \quad (5)$$

Here $|A_{th}|$ is the amplitude threshold that can be selected based on the noise floor level, $C_1$ and $C_3$ are constants, and the factor $\alpha$ is chosen arbitrarily to obtain the desired behavior of the weighting function as a function of signal amplitude level. The weighting function can also be defined such that it is has a sharp cut-off at a given threshold as shown in the equation below:

$$F(|A_{jk}(z)|,|A_{j+1k}(z)|)=0; \text{ if } \min(|A_{jk}(z)|,|A_{j+1k}(z)|)<|A_{th}|$$

$$F(|A_{jk}(z)|,|A_{j+1k}(z)|)=C_4(|A_{jk}(z)|\cdot|A_{j+1k}(z)|-|A_{th}|^2)^\alpha; \text{ if } \min(|A_{jk}(z)|,|A_{j+1k}(z)|)\geq|A_{th}| \quad (6).$$

Here $C_4$ is a constant, and the weighting function acts similar to a step-like function with a sharp transition at a given amplitude threshold, $|A_{th}|$. In another variation, the weighting function can be defined as follows:

$$F(|A_{jk}(z)|, |A_{j+1k}(z)|) = 0; \text{ if } \min(|A_{jk}(z)|, |A_{j+1k}(z)|) < |A_{th}| \quad (7)$$

$$F(|A_{jk}(z)|, |A_{j+1k}(z)|) = C_1 \log 10\left(\frac{|A_{jk}(z)| \cdot |A_{j+1k}(z)|}{|A_{th}|^2}\right);$$

$$\text{if } \min(|A_{jk}(z)|, |A_{j+1k}(z)|) \geq |A_{th}|.$$

In yet another embodiment, in order to explore a slightly different contrast variation, a generalized formulation for normalized intensity weighted variable power absolute standard deviation of Doppler imaging can be given as follows:

$$\frac{\sum_{j=1}^{N-1} F(|A_{jk}(z)|, |A_{j+1k}(z)|) \cdot |\Delta\phi_{jk}(z, t_{jk}) - \overline{\Delta\phi(z)}|^\gamma}{C_2 + \sum_{j=1}^{N-1} F(|A_{jk}(z)|, |A_{j+1k}(z)|)}. \quad (8)$$

Here, $\gamma$ is the factor responsible for variable power absolute standard deviation of Doppler imaging. In another embodiment, nonlinear intensity weighted absolute phase difference can also be used for obtaining motion contrast.

Figure 4:
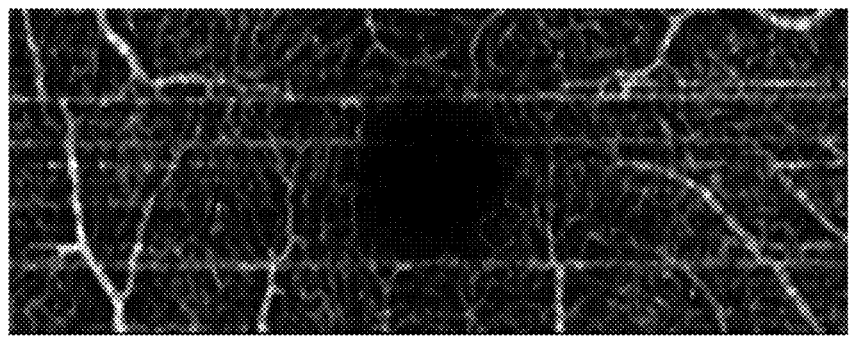
FIG. 4 shows two en face vasculature images processed using different motion contrast techniques. Panel A shows an image generated using nonlinear intensity weighted phase variance techniques of the present invention while Panel B shows an image generated using a Prior Art technique.
Figure 4:
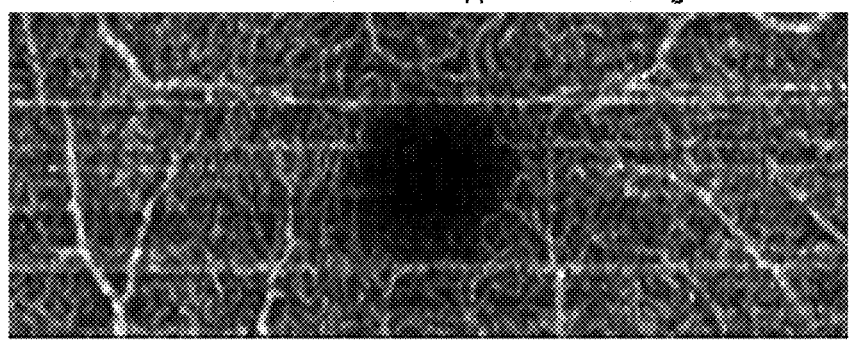

The relationship between the OCT signal amplitude and the associated phase errors is nonlinear and hence a nonlinear intensity weighted approach is required to obtain the best results. The final formula used by Chen et al. shown in Equation 2 uses a form of linear intensity weighting function. FIG. 4 shows the comparison of en face vasculature images obtained for a human retina (FOV 3 mm×1.2 mm) by using the Nonlinear Intensity Weighted Phase Variance of the present invention (A: top image) and the method described by Chen et al. (B: bottom image) using Equation 2. In order to generate an en face image of the vasculature from the motion-contrast data cube, a range of 25-30 pixels corresponding to 50-60 microns of tissue depth from the surface of internal limiting membrane (ILM) in retina as described above. The weighting function used for this simulation was of the form described in Equation 5. It can be clearly noticed from FIG. 4 that the nonlinear intensity weighted phase variance technique provides superior motion contrast images compared to the linear weighting method.

II. Vector Difference Method for Motion Contrast

In a preferred embodiment of the present invention, the difference of complex valued OCT signal is calculated from an inter-frame comparison. In vector difference method, the difference between two OCT measurements is calculated as follows:

$$\Delta A_{jk}(z,t_{jk})=A_{j+1k}(z,t_{j+1k})-A_{jk}(z,t_{jk}).$$

It must be noted that this difference method does not depend solely on intensity or phase variations alone. In order to correct for the phase offsets due to bulk motion or axial displacements, bulk-motion correction algorithms can be applied in a way similar to the methods described by J. F. deBoer et al. and Yasuno et al. (see references Yasuno et al., "Optical Coherence Angiography," Optics Express, 14(17), 7821-7840 (2006), and R. B. White et al., "In vivo dynamic human retinal blood flow imaging using ultra-high-speed spectral domain optical Doppler tomography," Optics Express, 11(25), 3490-3497 (2003)).

In one embodiment of the present invention, the absolute value of the difference can be calculated and averaged over multiple difference pairs. For example, if four B-scan measurements are obtained at the same location, then the motion contrast based on absolute vector difference pairs can be calculated as:

$$\frac{|\Delta A_{1k}| + |\Delta A_{2k}| + |\Delta A_{3k}|}{3},$$

$$\text{where } |\Delta A_{jk}(z, t_{jk})| = |A_{j+1k}(z, t_{j+1k}) - A_{jk}(z, t_{jk})|.$$

In another embodiment, the variance of the absolute vector difference pairs can be calculated to obtain motion contrast data.

III. Normalized Vector Difference Amplitude for Motion Contrast

In this method, the difference of normalized complex OCT signal is calculated from inter-frame comparison. The difference is calculated as follows:

$$\Delta U_{jk}(z, t_{jk}) = e^{i\phi_{j+1k}(z,t_{jk}+T)} - e^{i\phi_{jk}(z,t_{jk})} =$$

$$\sin\left(\frac{\phi_{j+1k}(z, t_{jk} + T) - \phi_{jk}(z, t_{jk})}{2}\right) e^{-i\left(\frac{\phi_{j+1k}(z,t_{jk}+T)-\phi_{jk}(z,t_{jk})}{2} - \frac{\pi}{2}\right)}.$$

The variance of the normalized vector difference of the N measurements can be shown by the following expression:

$$\frac{\sum_{j=1}^{N-1} (\Delta U_{jk}(z, t_{jk}) - \overline{\Delta U}) \cdot (\Delta U_{jk}(z, t_{jk}) - \overline{\Delta U})^*}{(N-1)} = \quad (9)$$

$$\frac{\sum_{j=1}^{N-1} |\Delta U_{jk}(z, t_{jk}) - \overline{\Delta U}|^2}{(N-1)}.$$

It can be seen that the amplitude of the difference vector is proportional to the sine of the phase difference divided by two. If we calculate the variance of the vector difference amplitude, it can also provide us with a means to detect motion contrast as shown by the following expression:

$$\frac{\sum_{j=1}^{N-1}\left(\sin\left(\frac{\Delta\phi_{jk}(z,t_{jk})}{2}\right)-\sin\left(\frac{\overline{\Delta\phi(z)}}{2}\right)\right)^2}{N-1}. \quad (10)$$

Figure 5:
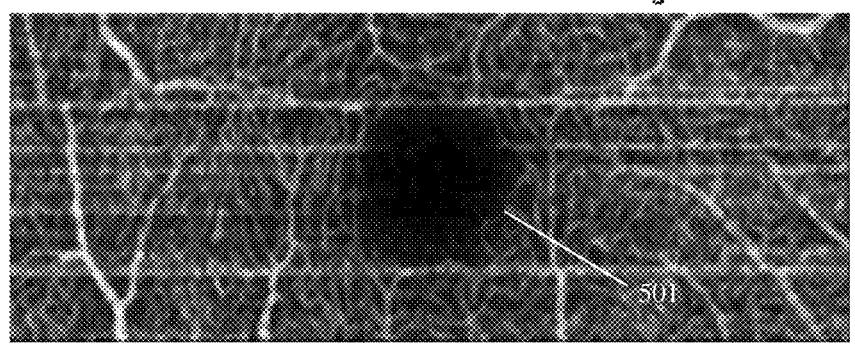
FIG. 5 shows an en face vasculature image generated using normalized vector difference variance imaging, another motion contrast technique of the present invention.

The advantage of using these methods over phase variance is that they enhance the contribution of small variations in phase measurements. Hence the sensitivity towards detection of micro-capillaries with smaller signal is improved further. FIG. 5 shows the image obtained by normalized vector difference vector variance (NVDV-variance) obtained for a human eye (FOV 3 mm×1.2 mm) by summing a 50 micron thick layer below ILM. It can be seen from the image in FIG. 5 that this technique enhances the detection of micro-capillaries near the avascular foveal zone 501.

IV. Non-Linear Intensity Weighted Variance of Normalized Vector Difference Amplitude for Motion Contrast In this method, the effect of errors in measurements of normalized vector difference amplitudes due to low SNR noise is reduced by using an intensity based weighting factor similar to the method described in Section I. The implementation of the method of applying intensity based weighting factors can be explained by the following two expressions:

$$\frac{\sum_{j=1}^{N-1}F(|A_{jk}(z)|,|A_{j+1k}(z)|)\cdot|\Delta U_{jk}(z,t_{jk})-\overline{\Delta U}|^2}{C_2+\sum_{j=1}^{N-1}F(|A_{jk}(z)|,|A_{j+1k}(z)|)}; \text{ and} \quad (11)$$

$$\sum_{j=1}^{N-1}F(|A_{jk}(z)|,|A_{j+1k}(z)|)\cdot \quad (12)$$

$$\frac{\left(\sin\left(\frac{\Delta\phi_{jk}(z,t_{jk})}{2}\right)-\sin\left(\frac{\overline{\Delta\phi(z)}}{2}\right)\right)^2}{C_2+\sum_{j=1}^{N-1}F(|A_{jk}(z)|,|A_{j+1k}(z)|)}.$$

As described earlier, the intensity based weighting function can be described in several ways including the examples shown in eqns. 2-4.

V. Other Methods for Motion Contrast Detection
Absolute Standard Deviation of Doppler Signal for Motion Contrast In this method, absolute standard deviation of Doppler signal is calculated instead of variance. The calculations are as follows:

$$\sigma_{abs}(\Delta\phi_{jk}(z,t_{jk}))=\frac{\sum_{j=1}^{N-1}|\Delta\phi_{jk}(z,t_{jk})-\overline{\Delta\phi(z)}|}{N}$$

The data obtained by this method can be rescaled non-linearly to improve the contrast.

Variable Power Absolute Standard Deviation of Doppler Imaging

In a more generalized form, any power of absolute phase difference can be summed to evaluate and improve the contrast variations in the final image. The calculations for this method are as follows:

$$\sigma_{abs}(\Delta\phi_{jk}(z,t_{jk}))|_{\gamma}=\frac{\sum_{j=1}^{N-1}|\Delta\phi_{jk}(z,t_{jk})-\overline{\Delta\phi(z)}|^{\gamma}}{N}.$$

Here Doppler absolute standard deviation (DASD) imaging and Doppler variance imaging are special cases of this method when gamma is equals to 1 ($\gamma=1$) and 2 ($\gamma=2$), respectively.

Doppler Root Mean Square Imaging

Calculation of RMS of Doppler signal is also a measure of motion contrast and can be used for vasculature imaging.

Figure 6:
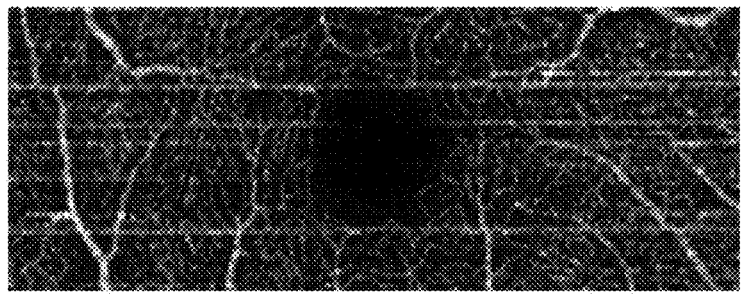
FIG. 6 illustrates the advantage filtering can have on en face vasculature images. Panel A is unfiltered while Panel B is filtered using a median filter approach.
Figure 6:
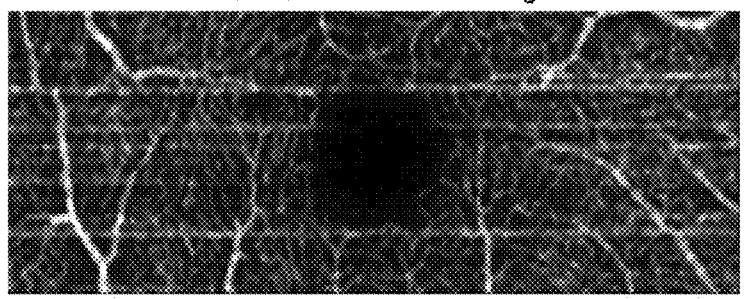

VI. Image Processing Techniques to Enhance Visualization of En Face Vasculature Images Image processing techniques like spatial digital filtering, adjustment of brightness and contrast, and non-linear rescaling of the image data can be used to further enhance the visualization of en face vasculature images. For example, FIG. 6 shows the difference between unfiltered (A: top image) and digitally filtered images (B: bottom image) of a human eye (FOV 3 mm×1.2 mm). In this figure, median filtering is used to smooth out the image. However, any other image resizing and spatial digital filtering techniques used to enhance the visualization of the image are all possible embodiments of this invention. It should be noted that all the previous images displayed were post-processed and digitally filtered to improve visualization of vasculature.

Figure 7:
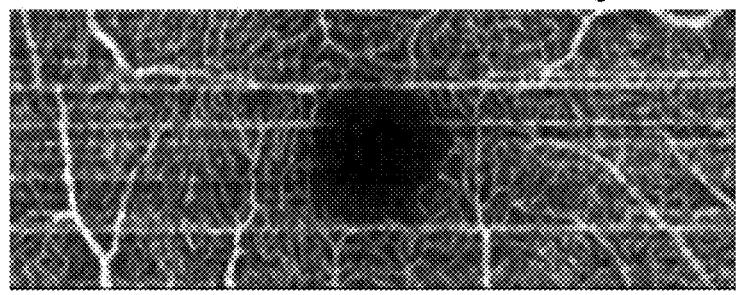
FIG. 7 illustrates the advantage scaling can have on en face vasculature images. Panel A is rendered at normal scale while Panel B is rendered at a scaling factor of 1.6.
Figure 7:
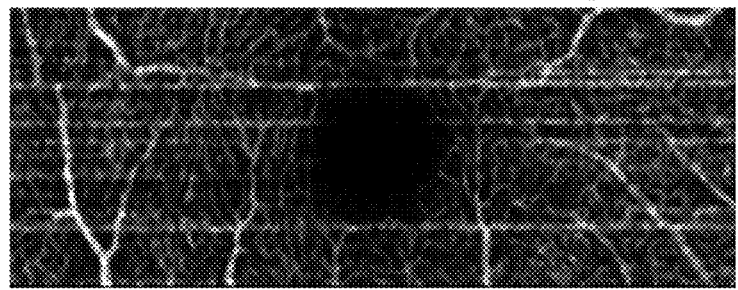

Nonlinear rescaling of the final image data can also be applied to obtain a desired contrast behavior as described by the following equation: $I_{NL}(x, y)=[I(x, y)]^{\gamma_{NL}}$. Here $\gamma_{NL}$ is a positive constant responsible for nonlinear scaling of image pixel intensity data ($I(x, y)$). FIG. 7 shows an example where a nonlinear scaling factor of 1.6 has been used to change the visualization of a vasculature image generated using normalized vector difference variance as described above. The top frame shows the unscaled version of the image while the bottom frame shows the scaled version.

Although various embodiments that incorporate the teachings of the present invention have been shown and described in detail herein, those skilled in the art can readily devise many other varied embodiments that still incorporate these teachings and may not require all of the above described elements to fall within the scope of the invention. While the description has focused on applying various motion contrast techniques to vasculature imaging of the eye, the systems and methods of the present invention could apply to other anatomical locations in which it is desirable to measure motion or flow.

The following references are hereby incorporated by reference:

US Patent Literature

U.S. Pat. No. 6,549,801 Chen et al. "Phase-resolved optical coherence tomography and optical Doppler tomography for imaging fluid flow in tissue with fast scanning speed and high velocity sensitivity"

U.S. Pat. No. 7,359,062 Chen et al. "High speed spectral domain functional optical coherence tomography and optical Doppler tomography for in vivo blood flow dynamics and tissue structure"

U.S. Pat. No. 7,301,644 Knighton et al. "Enhanced optical coherence tomography for anatomical mapping"

US Publication No. 2008/0025570 Fingler et al. "Dynamic motion contrast and transverse flow estimation using OCT,"

US Publication No. 2010/0027857 Wang "In vivo structural and flow imaging"

International Patent Literature

WO 2010/129494 Wang et al "Method and apparatus for quantitative imaging of blood perfusion in living tissue"

WO 2011/097631 Wang "Method and apparatus for ultrahigh sensitive optical microangiography"

Non-Patent Literature

S. Yazdanfar "Imaging and velocimetry of the human retinal circulation with color Doppler OCT," Optics Letters 25, 1448-1450 (2000).

R. A. Leitgeb et al., "Real-time assessment of retinal blood flow with ultrafast acquisition by color Doppler FDOCT," Optics Express, 11, 3116-3121 (2003).

Y. Zhao et al., "Doppler standard deviation imaging for clinical monitoring of in vivo human skin blood flow," Optics Letters 25, 1358-1360 (2000).

Makita et al., "Optical Coherence Angiography," Optics Express, 14(17), 7821-7840 (2006).

R. K. Wang et al., "Three dimensional optical angiography," Optics Express 15, 4083-4097 (2007).

L. An et al., "In vivo volumetric imaging of vascular perfusion within human retina and choroids with optical microangiography," Optics Express 16, 11438-11452 (2008).

R. K. Wang et al., "Depth-resolved imaging of capillary networks in retina and choroid using ultrahigh sensitive optical microangiography," Optics Letters, 35(9), 1467-1469 (2010).

L. An et al., "Ultrahigh sensitive optical microangiography for in vivo imaging of microcirculations within human skin tissue beds," Optics Express, 18(8), 8220-8228 (2010).

J. Fingler et al., "Mobility and transverse flow visualization using phase variance contrast with SD-OCT," Optics Express 15, 12636-12653 (2007).

J. Fingler et al., "Volumetric microvascular imaging of human retina using OCT with a novel motion contrast technique," Optics Express 17, 22190-22200 (2009).

J. M. Schmitt, "OCT elastography: imaging microscopic deformation and strain of tissue," Optics Express 3, 199-211 (1998).

S. J. Kirkpatrick et al., "OCT-based elastography for large and small deformations," Optics Express 14, 11585-11597 (2006).

A. Mariampillai et al., "Optimized speckle variance OCT imaging of microvasculature," Optics Letters 35, 1257-1259 (2010).

R. A. Leitgeb et al., "Ultrahigh resolution Fourier domain optical coherence tomography," Optics Express 12(10): 2156 (2004).

B. R. White et al., "In vivo dynamic human retinal blood flow imaging using ultra-high-speed spectral domain optical Doppler tomography," Optics Express, 11(25), 3490-3497 (2003).

G. Liu et al., "Intensity-based modified Doppler variance algorithm: application to phase instable and phase stable optical coherence tomography systems" Optics Express 19(12), 11429-11440 (2011).

L. Wang et al., "Frequency domain phase-resolved optical Doppler and Doppler variance tomography" Optics Communications 242 345-350 (2004).

S. Zotter et al., "Visualization of microvasculature by dual-beam phase-resolved Doppler optical coherence tomography" Optics Express 19(2) 1217-1227 2011.

S. Makita et al., "Comprehensive in vivo micro-vascular imaging of the human eye by dual-beam-scan Doppler optical coherence angiography" Optics Express 19(2) 1271-1283 2011.

What is claimed is:

1. An optical coherence tomography (OCT) system for determining localized motion in a sample, the OCT system including a light source, a sample arm, a reference arm and a detection arm, said system comprising:
   optics for scanning the light source over a plurality of lateral (X and Y) locations on the sample;
   a detector coupled to the detection arm for generating output signals in response to light collected from the sample arm and reference arm at each X and Y location; and
   a processor for controlling the scanning optics and for receiving the output signals generated by the detector, said processor operating to acquire at least two output signals from approximately the same location on the sample at two different times, generating complex OCT signals from the output signals, said complex signals being described by an intensity and phase, said processor further for normalizing the complex signals, taking the difference between at least two normalized complex OCT signals acquired at approximately the same location on the sample at two different times to generate motion contrast information.

2. An OCT system as recited in claim 1 further including a display for displaying the motion contrast information.

3. An OCT system as recited in claim 1, wherein the processor determines the amplitude value of the difference to generate the motion contrast information.

4. An OCT system as recited in claim 3, wherein the processor collects more than two output signals from approximately the same location on the sample, determines multiple differences between said output signals, and calculates the variance of the amplitudes of the multiple differences to determine the motion contrast information.

5. An OCT system as recited in claim 3, wherein the processor collects more than two output signals from approximately the same location on the sample, determines multiple differences between said output signals, and calculates the average of the amplitudes of the multiple differences to determine the motion contrast information.

6. An OCT system as recited in claim 1, wherein the at least two output signals are from successive B-scans.

7. An OCT system as recited in claim 1, wherein the at least two output signals are separated in time by approximately 2 to approximately 20 milliseconds.

8. An OCT system as recited in claim 1, wherein the processor collects more than two output signals at approximately the same location on the sample and takes the differences between the multiple output signals.

9. An OCT system as recited in claim 1, wherein the processor comprises a local and an external processor with the functions of controlling the scanning optics, acquiring at least two output signals, generating complex OCT signals, normalizing the complex signals, and taking the difference between at least two normalized complex OCT signals being divided between the two processors.

10. An optical coherence tomography (OCT) system for determining localized motion in a sample, the OCT system including a light source, a sample arm, a reference arm and a detection arm, said system comprising:
    optics for scanning the light source over a plurality of lateral (X and Y) locations on the sample;
    a detector coupled to the detection arm for generating output signals in response to light collected from the sample arm and reference arm at each X and Y location; and a processor for controlling the scanning optics and for receiving the output signals generated by the detector, said processor operating to acquire at least two output signals from approximately the same location on the sample at two different times, said processor determining motion contrast information using the at least two output signals from approximately the same location on the sample, said processor applying a nonlinear intensity based weighting function to the determined motion contrast information to reduce measurement errors.

11. An OCT system as recited in claim 10 further including a display for displaying the determined motion contrast information after the nonlinear intensity based weighting function has been applied.

12. An OCT system as recited in claim 10, wherein the processor determines the motion contrast information by using phase difference values between output signals taken at approximately the same locations on the sample.

13. An OCT system as recited in claim 12, wherein the processor sums the weighted motion contrast information.

14. An OCT system as recited in claim 13, wherein the processor uses the following equation to process the output signals:

$$\frac{\sum_{j=1}^{N-1} F(|A_{jk}(z)|, |A_{j+1k}(z)|) \cdot (\Delta\phi_{jk}(z, t_{jk}) - \overline{\Delta\phi(z)})^2}{C_2 + \sum_{j=1}^{N-1} F(|A_{jk}(z)|, |A_{j+1k}(z)|)}$$

wherein $\Delta\phi_{jk}(Z,t_{jk})$ is the phase difference value between two output signals, $\overline{\Delta\phi(z)}$ is the mean of phase difference values, $|A_{jk}(Z)|$ is the signal intensity of a given output signal, $F(|A_{jk}(z)|,|A_{j+1k}(z)|)$ is the signal intensity based weighting function and $C_2$ is a constant.

15. An OCT system as recited in claim 10, wherein the processor determines the motion contrast information by calculating the absolute value of phase difference values using the at least two output signals from approximately the same location.

16. An OCT system as recited in claim 15, wherein the processor uses the absolute value of the phase differences to generate an image of the motion contrast information.

17. An OCT system as recited in claim 10, wherein the at least two output signals are from successive B-scans.

18. An OCT system as recited in claim 10, wherein the at least two output signals are separated in time by approximately 2 to approximately 20 milliseconds.

19. An OCT system as recited in claim 10, wherein the processor determines the motion contrast information by calculating the absolute standard deviation of phase difference values of the at least two output signals from approximately the same location.

20. An OCT system as recited in claim 10, wherein the processor determines the motion contrast information by calculating the root mean square of phase difference values of the at least two output signals from approximately the same location.

21. An OCT system as recited in claim 10, wherein the processor determines the motion contrast information by taking the difference of normalized complex OCT signals corresponding to the at least two output signals.

22. An OCT system as recited in claim 21, wherein the processor takes the difference between the two normalized complex OCT signals using the following equation:

$$\Delta U_{jk}(z,t_{jk}) = e^{i\phi_{j+1k}(z,t_{jk}+T)} - e^{i\phi_{jk}(z,t_{jk})}$$

wherein $e^{i\phi_{jk}}(z,t^{jk})$ denotes the normalized complex OCT signal.

23. An OCT system as recited in claim 22, wherein the processor sums the weighted motion contrast information and stores or displays the sum.

24. An OCT system as recited in claim 23, wherein the processor uses the following equation to process the output signals:

$$\frac{\sum_{j=1}^{N-1} F(|A_{jk}(z)|, |A_{j+1k}(z)|) \cdot |\Delta U_{jk}(z, t_{jk}) - \overline{\Delta U}|^2}{C_2 + \sum_{j=1}^{N-1} F(|A_{jk}(z)|, |A_{j+1k}(z)|)}$$

wherein $|A_{jk}(z)|$ is the signal intensity of a given output signal, $F(|A_{jk}(z)|,|A_{j\pm 1k}(z)|)$ is the signal intensity based weighting function, $\overline{\Delta U}$ is the mean of the normalized complex OCT values, and $C_2$ is a constant.

25. An OCT system as recited in claim 10, wherein the processor comprises a local and an external processor with the functions of controlling the scanning optics, acquiring at least two output signals, determining motion contrast information using the at least two output signals and applying a nonlinear intensity based weighting function to the determined motion contrast information being divided between the two processors.

* * * * *